United States Patent
Saito et al.

[11] Patent Number: 5,891,097
[45] Date of Patent: Apr. 6, 1999

[54] ELECTROCHEMICAL FLUID DELIVERY DEVICE

[75] Inventors: Satoshi Saito; Yoshinori Tanaka; Yuko Fujita, all of Kyoto, Japan

[73] Assignee: Japan Storage Battery Co., Ltd., Kyoto, Japan

[21] Appl. No.: 513,619

[22] Filed: Aug. 10, 1995

[30] Foreign Application Priority Data

Aug. 12, 1994 [JP] Japan .................................. 6-211927

[51] Int. Cl.⁶ .................................................. A61M 37/00
[52] U.S. Cl. ........................ 604/141; 604/133; 604/132; 604/131
[58] Field of Search ..................... 604/131–133, 604/141, 145–147, 143

[56] References Cited

U.S. PATENT DOCUMENTS

| | | | |
|---|---|---|---|
| 3,993,069 | 11/1976 | Buckles et al. | 604/132 |
| 4,496,343 | 1/1985 | Prosl et al. | 604/131 |
| 4,522,698 | 6/1985 | Maget . | |
| 4,902,278 | 2/1990 | Maget et al. . | |
| 5,090,963 | 2/1992 | Gross et al. | 604/145 |
| 5,163,909 | 11/1992 | Stewart | 604/131 |
| 5,167,631 | 12/1992 | Thompson et al. | 604/132 |
| 5,242,406 | 9/1993 | Gross et al. | 604/132 |
| 5,257,987 | 11/1993 | Athayde et al. | 604/131 |
| 5,290,240 | 3/1994 | Horres, Jr. | 604/131 |
| 5,368,571 | 11/1994 | Horres, Jr. | 604/131 |
| 5,398,851 | 3/1995 | Sancoff et al. | 222/386.5 |
| 5,578,005 | 11/1996 | Sancoff et al. | 604/132 |

FOREIGN PATENT DOCUMENTS

| | | |
|---|---|---|
| 58-48209 | 10/1983 | Japan . |
| 2-302264 | 12/1990 | Japan . |

*Primary Examiner*—Robert A. Clarke
*Assistant Examiner*—David J. Cho
*Attorney, Agent, or Firm*—Sughrue, Mion, Zinn, Macpeak & Seas, PLLC

[57] ABSTRACT

A fluid delivery device according to the present invention has a fluid delivery device body and an electrochemical cell portion for generating a gas when supplied with a DC current. The fluid delivery device body has a partition member transformable by the pressure of a gas, and a gas introduction portion. A first compartment and a second compartment are formed in the fluid delivery device body by the partition member, and a gas generated in the electrochemical cell portion is introduced into the second compartment through the gas introduction portion. A transformable fluid reservoir having a fluid delivery portion is disposed in the first compartment. If the gas generated in the electrochemical cell portion is introduced into the second compartment, the inner pressure of the second compartment increases, and the partition member is pushed, so that a fluid in the fluid reservoir disposed in the first compartment is delivered from the fluid delivery portion.

1 Claim, 4 Drawing Sheets

ELECTROCHEMICAL FLUID DELIVERY DEVICE

BACKGROUND OF THE INVENTION

1. Field of the Invention

The present invention relates to a fluid delivery device such as an infusion pump to deliver a fluid with high accuracy.

2. Description of the Related Art

Recently, various infusion pumps have come into use in order to infuse a liquid medicine into human bodies little by little with high accuracy.

Conventional infusion pumps can be classified into four kinds in accordance with the difference in their systems, that is, a syringe pump, a peristaltic (rotor) pump, a finger pump and a bellows pump. Of these, any other than the bellows pump use a motor such as a stepping motor, a rotary solenoid motor, a DC motor, or the like, as a driving source for ejecting a liquid medicine, and adopt a complicated mechanism for controlling the infuse volume of the liquid medicine. Generally, such pumps are therefore heavy in weight and large in size and hence expensive. Therefore, such pumps are usually used on a bedside in a hospital, and are unsuitable for portable or disposable use.

On the other hand, a bellows pump is of a system in which bellows are pushed by use of vaporization pressure of a freon gas to thereby infuse a liquid medicine. However, it is difficult to control the vaporization pressure of the freon gas. Further, this pump has another problem related to the accuracy of the infusion particularly when a very small amount of the liquid medicine is infused over a long period.

One of the present inventors has proposed a device having a pumping function and a gas flow control function in which an electrochemical cell is used for generating an amount of gas which is proportional to the value of a DC current supplied thereto (Japanese Patent No. 1214001). Recently, an electrochemically driven drug dispenser using the principle of the above device has been proposed (H. J. R. Maget, U.S. Pat. No. 4,522,698). This electrochemically driven drug dispenser has an electrochemical cell in which porous gas diffusion electrodes are joined respectively to the opposite surfaces of an ion exchange membrane containing water functioning as an electrolyte. The electrochemically driven drug dispenser uses such a phenomenon that when hydrogen is supplied to an anode of the electrochemical cell and a DC current is made to flow between the anode and the cathode, the hydrogen becomes hydrogen ions at the anode, and when the produced hydrogen ions reach the cathode through the ion exchange membrane, an electrochemical reaction arises to generate hydrogen thereat. That is, the hydrogen generated and pressurized at the cathode is used as a driving source for pushing a piston, a diaphragm, bellows or the like. Alternatively, oxygen may be used in place of hydrogen as a reactor in this electrochemical cell. If the air is used as source of oxygen to be supplied to the cathode, the structure of the drug dispenser may be made considerably simple.

Further, another method has been proposed using electrolysis of water (Unexamined Japanese Patent Publication No. Hei.2-302264), which is an improved type of such an electrochemically driven drug dispenser. In this method, water is contained in an electrochemical cell in which a cathode and an anode are integrally joined to the opposite surfaces of an ion exchange membrane respectively, or a cathode and an anode are joined both onto one of the opposite surfaces of an ion exchange membrane, so that the cathode and the anode are separated and insulated from each other. Thus, hydrogen, oxygen, or a gas mixture of hydrogen and oxygen generated by electrolysis of water when a DC current is made to flow between the electrodes is used as a pressurization source of the drug dispenser.

When a liquid medicine is infused by an electrochemically driven drug dispenser, there is a method in which the liquid medicine with a predetermined volume is put into a vessel provided with a flexible diaphragm, and the diaphragm is then pushed by the pressure of a gas so as to infuse the liquid medicine. As a specific example of this method, a structure has been proposed in which a flexible diaphragm is disposed in a part of an annular vessel, a liquid medicine is put into a vessel portion surrounded by a wall portion of the vessel and the flexible diaphragm, and a gas generated from an electrochemical cell is supplied to a gap formed between another wall portion of the vessel and the flexible diaphragm to thereby infuse the liquid medicine (H. J. R. Maget, U.S. Pat. No. 4,902,278). In such a structure, when different kinds of liquid medicines are used in one device, it is necessary to cleanse the inside of the vessel every time, and therefore only one kind of a liquid medicine can be used in one device in practical use.

As a practical matter, however, it is impossible to manufacture such a drug dispenser easily and inexpensively because of its complicated structure. In addition, particularly in the case where a liquid medicine is to be delivered, a disinfection or sterilization of the whose system is inevitable. This operation is very difficult to perform in the above-mentioned structure.

There has been further considered to a device in which a liquid medicine or blood is charged in advance into a fluid reservoir consisting of a flexible bladder having a fluid delivery pipe. This fluid reservoir is put into a closed vessel, and gas generated from an electrochemical cell is introduced into the closed vessel. The pressure in a space defined by the inner wall of the closed vessel and the outer surface of the bladder is increased to push the bladder to thereby deliver a fluid. In this device, when a disinfected fluid such as a liquid medicine, blood or the like is to be delivered into a human body, such a fluid must not come into contact with the air or the like at all. However, the consideration of sealing the vessel into which the fluid reservoir is received, or sealing the closed vessel in the condition that a fluid delivery pipe is led to the outside of the closed vessel is troublesome. For instance, an operation of screwing through an O-ring, or the like, is troublesome.

SUMMARY OF THE INVENTION

It is therefore an object of the present invention to solve the foregoing problems in an electrochemically driven drug dispenser, and to provide a fluid delivery device which is not expensive, has simple structure, and is easy to operate.

The fluid delivery device according to the present invention comprises a fluid delivery device body and an electrochemical cell portion. The electrochemical cell portion is capable of generating a gas when a DC current is supplied thereto. The fluid delivery device body has a partition member transformable by the pressure of a gas so that the first and the second compartments are formed in the fluid delivery device body. The fluid delivery device body further has a gas introduction portion for introducing a gas generated in the electrochemical cell portion into the second compartment. A transformable fluid reservoir having a fluid delivery portion is disposed inside the first compartment. The gas generated in the electrochemical cell portion is introduced into the second compartment so as to increase the inner pressure of the second compartment and press the partition member. Accordingly, the fluid reservoir is pressed by the partition member so that a fluid in the fluid reservoir is delivered out from the fluid delivery portion.

BRIEF DESCRIPTION OF THE DRAWINGS

In the accompanying drawings.

DETAILED DESCRIPTION OF THE INVENTION

The detailed description of the present invention will be described referring to the accompanying drawings as follows.

The most significant characteristic of the fluid delivery device according to the present invention is that a partition member, which is transformable by the pressure of a gas, is disposed inside of a fluid delivery device body so that the inside of the fluid delivery device body is partitioned into two kinds of compartments including a first compartment which is not necessary to be kept air-tight and a second compartment is kept air-tight.

When a gas generated upon supply of a DC current to an electrochemical cell portion is introduced into the second compartment which is kept air-tight, the pressure in the second compartment increases so that the partition member which is transformable by gas pressure and attached inside the fluid delivery device body is pressed toward the first compartment. With the transformation of the pressed partition member, the gas pressure is transmitted to a transformable fluid reservoir portion received in the first compartment. As a result, the fluid reservoir portion is pushed against the inner wall of the fluid delivery device body so that a fluid is delivered out from the fluid delivery portion.

The structure of the electrochemical fluid delivery device according to the present invention and the principle of operation thereof will be described with reference to FIG. 1A and FIG. 1B.

Figure 1A:
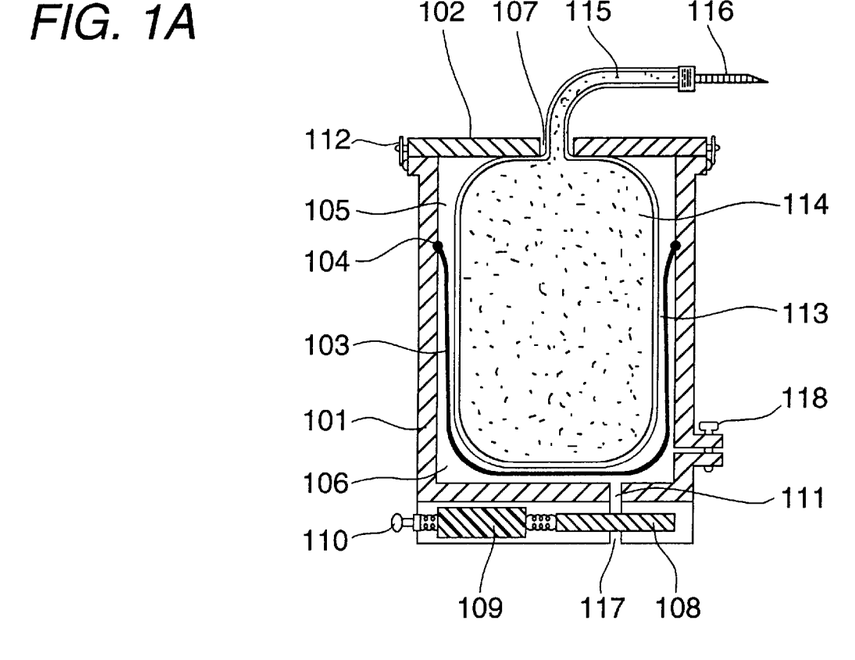
FIG. 1A is a sectional view of a fluid delivery device shown in Example 1 according to the present invention illustrating a state immediately before use of the fluid delivery device.
Figure 1B:
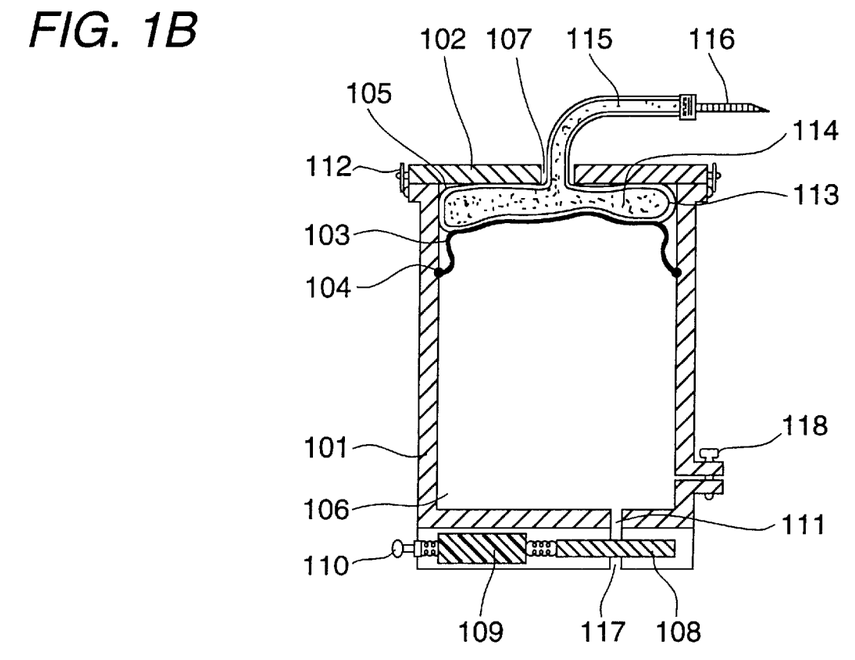
FIG. 1B is a sectional view of the fluid delivery device shown in Example 1 according to the present invention illustrating termination of the use of the fluid delivery device.

In FIG. 1A and FIG. 1B, reference numerals 101 and 102 represent a vessel body and a vessel cover, respectively. The fluid delivery device body is defined by the vessel body 101 and the vessel cover 102. A partition member 103 is flexible and capable of being transformed by gas pressure. The partition member 103 is attached to the inner surface of the vessel body 101.

The inside of the vessel body 101 is partitioned by the partition member 103 into a first compartment 105 and a second compartment 106. The first compartment 105 is a space defined by the partition member 103, the inner wall of the vessel body 101 and the inner wall of the vessel cover 102; and the second compartment 106 is a space defined by the partition member 103, the inner wall of the vessel body 101 and the inner wall of the bottom portion of the vessel body 101.

A hole 107 is provided in the vessel cover 102 in order to lead out a fluid delivery portion from the vessel. An electrochemical cell portion 108 is attached onto the bottom portion of the vessel body 101. Reference numerals 109 and 110 represent a power supply and a switch, respectively. A gas introduction portion 111 introduces a gas generated from the electrochemical cell portion 108 into the second compartment 106. The gas introduction portion 111 is provided as a passageway in the bottom portion of the vessel body 101. Consequently, the second compartment 106 is kept air-tight. Fittings 112 fixedly connect the vessel body 101 and the vessel cover 102 to each other. A transformable fluid reservoir 113 reserves a fluid 114 to be delivered therein. The reference numeral 115 represents a fluid delivery pipe as the fluid delivery portion; 116, an injection needle; 117, a hole for discharging gas to the outside; and 118, a valve for discharging gas accumulated in the second compartment 106 after the completion of use.

When this fluid delivery device is used, as shown in FIG. 1A, the fluid reservoir 113 reserving the fluid 114 therein is received in the first compartment 105 of the vessel body 101, and the fluid delivery pipe 115 is passed through the hole 107 formed in the vessel cover 102, so that the injection needle 116 is led to the outside of the vessel body 101. The vessel body 101 and the vessel cover 102 are fixedly connected to each other by the fittings 112. In this state, since the fluid reservoir 113 is filled with the fluid 114, the partition member 103 reaches a position near the bottom portion of the vessel body 101 by the weight of the fluid reservoir 113 itself so that the volume of the first compartment 105 is large while the volume of the second compartment 106 is small. Incidentally, it is not necessary to air-tightly block the gap between the vessel body 101 and the vessel cover 102 and the gap between the edge of the hole 107 formed in the vessel cover 102 and the fluid delivery pipe 115.

Next, the switch 110 is pushed so as to make a DC current flow from the power supply 109 to the electrochemical cell portion 108. When a water electrolytic cell is used as the electrochemical cell portion 108, the electrolytic reaction of water arises in the electrochemical cell portion 108. Therefore, if oxygen generated at the anode is introduced into the second compartment 106 through the passageway 111, the pressure of oxygen in the second compartment 106 increases so long as the current conduction is continued, because the second compartment 106 is kept air-tight. Assuming that the pressure of the atmosphere is 1 atm, the partition member 103 is pushed by the pressure of oxygen when the pressure in the second compartment 106 becomes a little higher than 1 atm, and the pushing force is transmitted to the fluid reservoir 113 filled with the fluid 114. Accordingly, the fluid reservoir 113 is pushed against the inner wall of the vessel cover 102 or the vessel body 101 so that the fluid 114 is delivered out from the injection needle 116 through the fluid delivery pipe 115 at a constant speed. The hydrogen generated from the electrochemical cell portion 108 is discharged to the outside through the hole 117.

FIG. 1B is a sectional view illustrating the state immediately before the completion of use. In this state, the second compartment 106 is filled with compressed oxygen, and the volume thereof has become large. On the other hand, the fluid reservoir 113 shrinks, and only a small amount of the fluid 114 remains, so that the volume of the first compartment 105 becomes small. If current conduction is further continued, the fluid 114 in the fluid reservoir 113 is exhausted, and the delivery of the fluid 114 is stopped automatically. After the completion of use, the valve 118 is opened manually so as to release oxygen accumulated in the second compartment 106, and thereafter the vessel cover 102 is opened to take out the fluid reservoir 113.

The electrochemical cell portion may be disposed separately from the fluid delivery device body. In such a case, a gas generated from the electrochemical cell portion is introduced into the second compartment of the fluid delivery device body through a gas introduction pipe such as a tube. The electrochemical cell portion may be formed integrally with the fluid delivery device body. In this case, a gas is introduced into the second compartment directly. The electrochemical cell portion may be provided by any other methods. In addition, the electrochemical cell portion may be designed so as to be detachable from the fluid delivery device body. In such a case, a gas is introduced into the second compartment directly, or through a gas introduction pipe.

The quantity of the gas generated from the electrochemical cell at a constant pressure depends on the quantity of electricity (current×time). That is, with respect to the quantity of electricity of 1 Ah, the theoretical value of the quantity of hydrogen gas is 420 ml (0° C. and 1 atm) and oxygen 210 ml (0° C. and 1 atm). The practical value of the quantity of the gas is 70 to 95% of its theoretical value because of the permeability of the gas, the recombination reaction of oxygen and hydrogen in the surface of an electrode, and the like. In addition, the practical value of the quantity of the gas depends on the variation of the operation current density. Further, the required size of the electrochemical cell portion depends, for example, on the set values of the delivery rate and the total quantity of a liquid medicine.

A DC current is necessary to actuate the electrochemical cell portion. It is necessary to supply a DC current to the electrochemical cell through a DC power supply from an AC power supply when it is necessary to deliver a comparative large amount of a fluid. On the other hand, when a comparative small amount of a fluid is to be delivered, for example, 50 ml of a fluid is to be delivered over 48 hours, a small-sized battery may be used as a power supply. In the case where such a small-sized battery is used, the fluid delivery device may be made portable if the battery and the electrochemical cell portion are mounted directly on the fluid delivery device body. Accordingly, when the device is used for medical treatment, a patient can move freely.

Although a fluid delivery device according to the present invention is optimum for delivering a liquid medicine to a patient, a gas can be delivered if a check valve is provided in a fluid delivery pipe. Therefore, the device may be applied to the delivery of a fluid or gas for industrial or any other use.

EXAMPLE 1

A fluid delivery device was produced, in which a water electrolytic cell using a solid polymer electrolyte was used as the electrochemical cell. FIG. 1A shows a sectional structure of the fluid delivery device immediately before use, and FIG. 1B shows the sectional structure immediately before the completion of the use. The vessel body 101 was made from polypropylene, and had an outer dimension which was 55 mm in width, 25 mm in depth and 140 mm in height. The vessel cover 102 made from polypropylene similar to the vessel body 101. Here, the fluid delivery device body includes the vessel body 101 and the vessel cover 102. The partition member 103 was flexible and capable of being transformed by the pressure of a gas. Here, as the partition member 103, a sheet made from polyethylene terephtalate (PET) having a thickness of 0.5 mm was used, and the sheet was attached to a position 104 which was 100 mm in height from the bottom portion of the inner surface of the vessel body 101.

The inside of the vessel body 101 was partitioned into the first compartment 105 and the second compartment 106 by the diaphragm 103 which was a partition member. The first compartment 105 was the space defined by the diaphragm 103 as the partition member, the inner wall of the vessel body 101 and the inner wall of the vessel cover 102. The second compartment 106 was the space defined by the diaphragm 103 as the partition member, the inner wall of the vessel body 101 and the inner wall of the bottom portion of the vessel body 101.

The hole 107 was formed through the vessel cover 102 in order to extract a fluid delivery portion from the vessel. The electrochemical cell portion 108 was a water electrolytic cell. In the electrochemical cell portion 108 as the water electrolytic cell, porous platinum electrodes having a diameter of 20 mm were joined by electroless plating to the both sides of a solid polymer protonic conductor having diameter of 30 mm, which was a solid electrolyte, so that the electrodes were made to act as an anode and a cathode respectively. The electrochemical cell portion 108 was attached integrally to the bottom portion of the vessel body 101. The power supply 109 was constituted by a combination of a battery and a constant current device with the switch 110.

The gas introduction portion introduces a gas generated from the electrochemical cell portion 108 into the second compartment 106. The gas introduction portion 111 was provided as a passageway in the bottom portion of the vessel body 101. The fittings 112 fixedly connects the vessel body 101 and the vessel cover 102 to each other. The transformable fluid reservoir 113 was a polyvinyl chloride bladder of 0.2 mm in thickness, in which about 110 ml of a physiological solution as the fluid 114 was reserved. The reference numeral 115 represents a fluid delivery pipe as a fluid delivery portion; and 116, an injection needle. The hole 117 was used for discharging hydrogen to the outside; and the valve 118 is used for discharging oxygen accumulated in the second compartment 106 after the completion of use.

When the fluid delivery device was used, as shown in FIG. 1A, first, the fluid reservoir 113 was received in the first compartment 105 of the vessel body 101, and the fluid delivery pipe 115 was passed through the hole 107 formed through the vessel cover 102 so that the injection needle 116 was led to the outside of the vessel body 101. The vessel body 101 and the vessel cover 102 were fixedly connected to each other by the fittings 112. It is preferable to make the fittings 112 simple enough so as to be operated just by pushing a button. In this example, the fluid reservoir 113 was filled with the physiological salt solution 114. Therefore, the diaphragm 103 was near the bottom portion of the vessel body 101 because of the increasing volume of the fluid reservoir 113 itself, so that the volume of the first compartment 105 was large while the volume of the second compartment 106 was small. The gap between the vessel body 101 and the vessel cover 102 and the gap between the hole 107 formed through the vessel cover 102 and the fluid delivery pipe 115 were not blocked. That is, the state was left such that the air may be admitted through the gaps.

Next, when the switch 110 was pushed so as to make a DC current of 600 mA to flow from the power supply 109 to the electrochemical cell portion 108, the electrolytic reaction of water arose in the electrochemical cell 108. Oxygen generated from the anode was introduced into the second compartment 106 through the passageway 111 so that the pressure of oxygen in the second compartment 106 increased with the continuation of the current conduction because the second compartment 106 was kept air-tight. Since the pressure of the atmosphere was 1 atm and the pressure in the second compartment 106 became a little higher than 1 atm, the diaphragm 103 was pushed by the pressure of oxygen so that the force is transmitted to the fluid reservoir 113 filled with the physiological salt solution 114. Accordingly, the fluid reservoir 113 was pushed against the inner wall of the vessel cover 102 or the vessel body 101 because the fluid reservoir 113 was made from polyvinyl chloride and therefore was soft. The physiological salt solution 114 was delivered from the injection needle 116 through the fluid delivery pipe 115 at the rate of 110 ml per hour.

FIG. 1B is a sectional view illustrating the state immediately before the completion of use. In this state, the second compartment 106 was filled with a compressed oxygen gas, and the volume thereof had become large. On the other hand, the volume of the fluid reservoir 113 shrank, only a small amount of the physiological salt solution 114 remained, and the volume of the first compartment 105 had become small. When current conduction was further continued, the physiological salt solution 114 in the fluid reservoir 113 was exhausted, and the delivery of the physiological salt solution 114 was stopped automatically. After the completion of use, the valve 118 was opened so as to release oxygen accumulated in the second compartment 106, and thereafter the vessel cover 102 was opened to take out the fluid reservoir 113. Although the valve 118 was opened manually after the completion of use in this example, a valve which is opened automatically at a predetermined pressure may be attached to release a gas such as oxygen, or the like automatically, or, alternatively, a pressure responsive automatically release valve may be provided.

In the case where hydrogen generated at the cathode is used instead of oxygen generated at the anode as the gas to be introduced into the second compartment 106 from the electrochemical cell portion 108, the current may be selected to be 300 mA. If both the oxygen and the hydrogen are to be introduced into the second compartment, the current may be selected to be 200 mA. In either case, the quantity of oxygen or hydrogen generated by electrolysis of water at a constant pressure depends on the quantity of electricity (current×time). Therefore, when a constant current is made to flow, the quantity of fluid to be delivered per unit time becomes constant. Accordingly, it is possible to establish a desired fluid delivery rate by changing the degree of the current to be made to flow.

EXAMPLE 2

Having the same structure as that of Example 1, a fluid delivery device was produced by use of a polyvinyl chloride sheet of 0.3 mm thick as the partition member 103 which was attached inside the vessel body 101 and which was transformable by the pressure of a gas. When a current similar to that in Example 1 was made to flow, a physiological salt solution was delivered at a similar rate.

EXAMPLE 3

Figure 2:
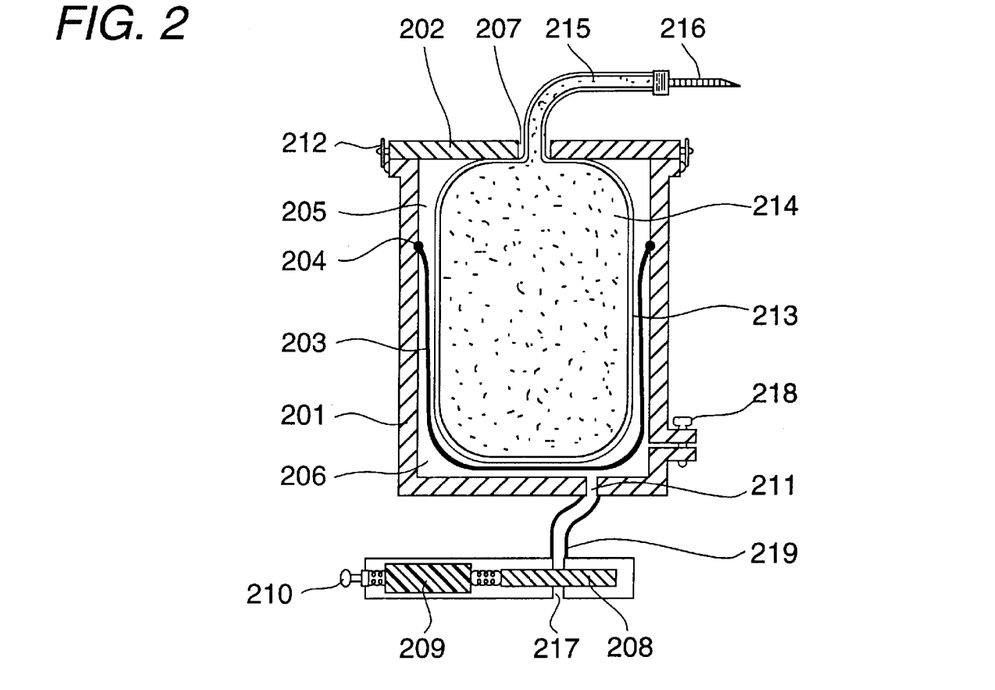
FIG. 2 is a diagram illustrating a sectional structure of a fluid delivery device shown in Example 3 according to the invention.

Having a structure similar to that of Example 1, a fluid delivery device was produced so that a vessel body and a unit including an electrochemical cell portion and a power supply were separated, and a gas generated from the electrochemical cell was introduced into a second compartment through a gas introduction pipe. FIG. 2 shows the sectional structure. In FIG. 2, the reference numeral 201 represents a vessel body; 202, a vessel cover; and 203, a partition member which was flexible and could be transformed by the pressure of a gas. The partition member 203 was attached to an appropriate position 204 inside the vessel body 201. The inside of the vessel body 201 was partitioned into a first compartment 205 and a second compartment 206 by the partition member 203. A hole 207 was formed through the vessel cover 202 in order to lead a fluid delivery portion out of the vessel. An electrochemical cell portion 208 was attached to the bottom portion of the vessel body 201. The reference numeral 209 represents a power supply; 210, a switch; and 211, a gas introduction portion for introducing a gas generated from the electrochemical cell portion 208 into the second compartment 206. The gas introduction portion 211 was provided as a passageway in the bottom portion of the vessel body 201. Fittings 212 was used for fixedly connecting the vessel body 201 and the vessel cover 202 to each other. A transformable fluid reservoir 213 reserved a physiological salt solution 214 therein. The reference numeral 215 represents a fluid delivery pipe as the fluid delivery portion; 216, an injection needle; 217, a hole for discharging gas to the outside; and 218, a valve for discharging a gas accumulated in the second compartment 206 after the completion of use. All the materials used herein were the same as those used in Example 1. A polyvinyl chloride tube having an outer diameter of 10 mm and an inner diameter of 8 mm was used as the gas introduction pipe 219. Although any of various materials such as a silicon tube, a polypropylene tube, or the like may be used other than the polyvinyl chloride tube as the gas introduction pipe 219, it is preferable to select a material having a low permeability to a generated gas. When a current exactly similar to that in Example 1 was made to flow, a physiological salt solution was delivered at the same rate.

EXAMPLE 4

Having a structure similar to that of Example 1, a fluid delivery device was produced so that hydrogen generated from a cathode of an electrochemical cell was absorbed into a hydrogen absorbing alloy.

Figure 3:
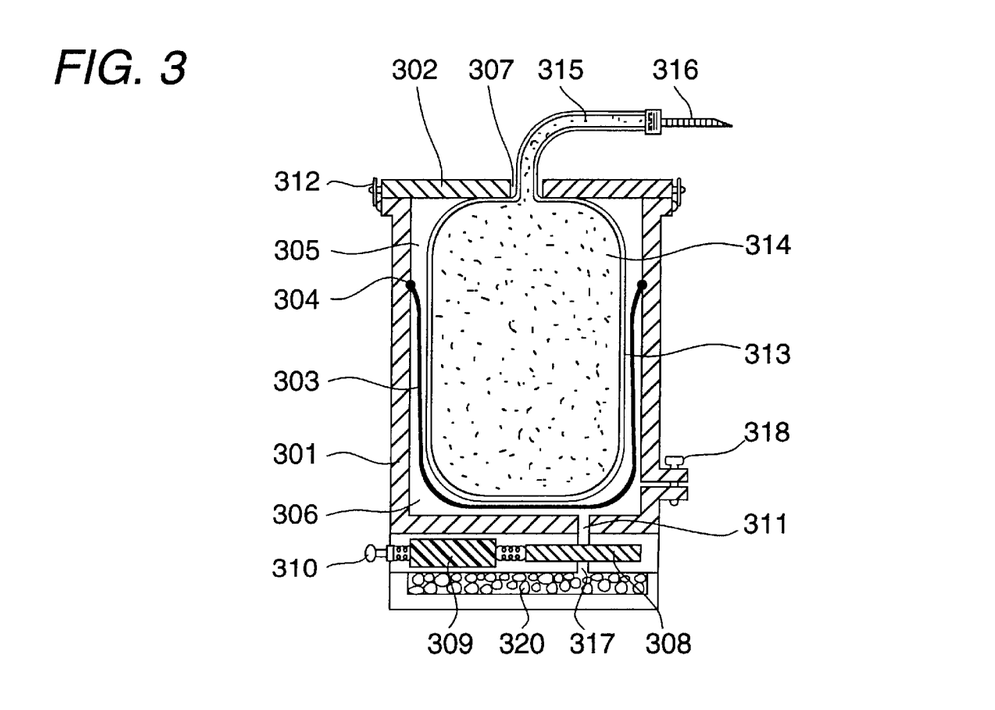
FIG. 3 is a diagram illustrating a sectional structure of a fluid delivery device shown in Example 4 according to the invention.

FIG. 3 shows the sectional structure. In FIG. 3, the reference numeral 301 represents a vessel body; 302, a vessel cover; and 303, a partition member which is flexible and can be transformed by the pressure of a gas. The partition member 303 was attached to an appropriate position 304 inside the vessel body 301. The inside of the vessel body 301 was partitioned by the partition member 303 into a first compartment 305 and a second compartment 306. A hole 307 was formed through the vessel cover 302 in order to lead a fluid delivery portion out of the vessel. An electrochemical cell portion 308 was attached to the bottom portion of the vessel body 301. The reference numeral 309 represents a power supply; 310, a switch; and 311, a gas introduction portion for introducing a gas generated from the electrochemical cell portion 308 into the second compartment 306. The gas introduction portion 311 was provided as a passageway in the bottom portion of the vessel body 301. Fittings 312 was used for fixedly connecting the vessel body 301 and the vessel cover 302 to each other. A transformable fluid reservoir 313 reserved a physiological salt solution 314 therein. The reference numeral 315 represents a fluid delivery pipe acting as the fluid delivery portion; 316, an injection needle; 317, a gas passageway; and 318, a valve for discharging gas accumulated in the second compartment 306 after the completion of use. All the materials used herein were the same as those used in Example 1. Lanthanum-nickel 5 hydride (LaNi$_5$) was used as a hydrogen absorbing alloy 320.

In the fluid delivery device, hydrogen generated from the cathode reached the hydrogen absorbing alloy 320 through the gas passageway 317, and absorbed into the hydrogen absorbing alloy 320. Accordingly, a physiological salt solution could be delivered without releasing any hydrogen to the outside of the device. As for the kind of the hydrogen absorbing alloy, it is possible to use any of various kinds of hydrogen absorbing alloys such as a misch metal, a titanium-nickel alloy hydride, and the like, other than the lanthanum-nickel 5 hydride.

EXAMPLE 5

Figure 1C:
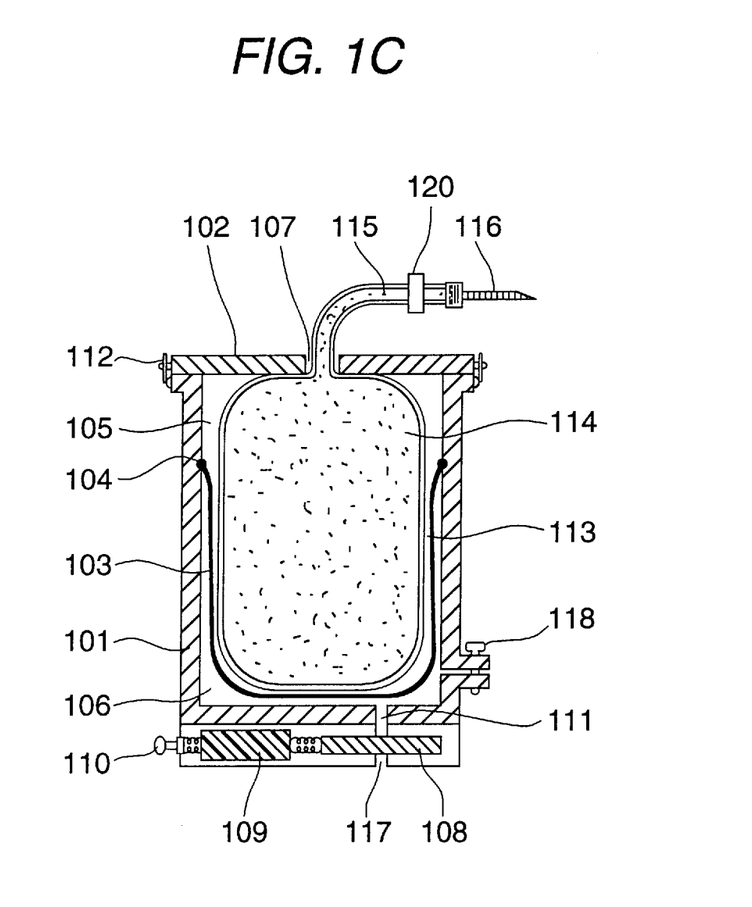
FIG. 1C is a sectional view of a fluid delivery device shown in Example 5 according to the present invention.

Having a structure similar to that of Example 1, a fluid delivery device was produced so that a check valve 120 was attached to the fluid delivery portion 115 as shown in FIG. 1C. In this device, there was no leakage of a fluid from the fluid delivery portion when the device was not used. In addition, back-flow could be prevented even if the back pressure from an injection needle was higher than the pressure in a fluid reservoir when the device was used. With this structure, a gas can be used instead of a liquid as a fluid.

EXAMPLE 6

Figure 4:
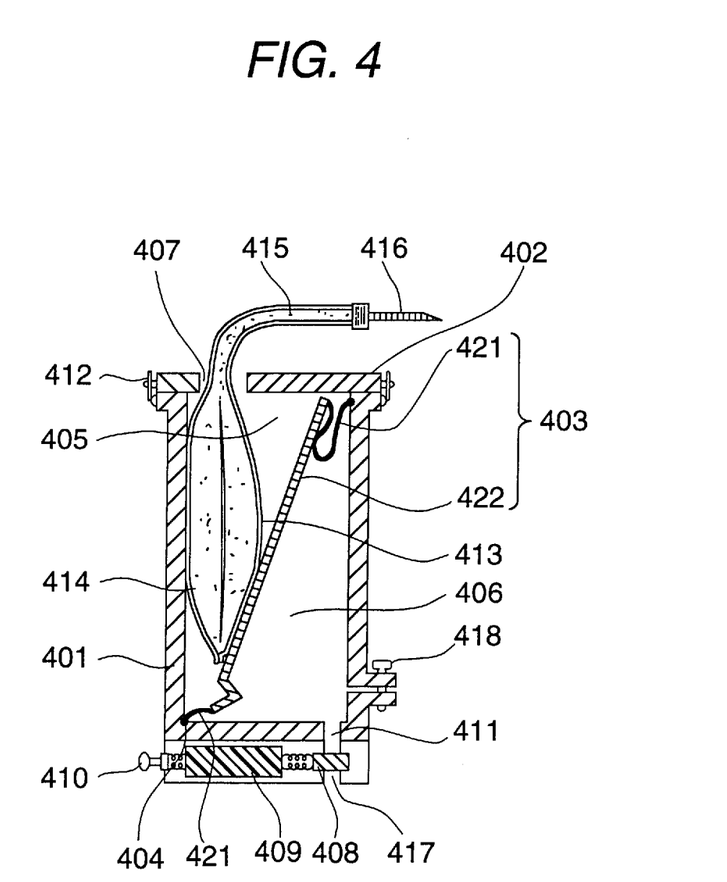
FIG. 4 is a sectional model diagram illustrating a structure of a partition member in Example 6 according to the present invention.

FIG. 4 shows a structure of another partition member. In FIG. 4, the reference numeral 401 represents a vessel body; and 402, a vessel cover; and 403, a partition member. The partition member 403 had a transformable portion 421 which could be transformed by the pressure of a gas, and a not-transformable plate 422. A polyvinyl chloride sheet of 0.3 mm thick was used as the transformable portion 421, and a polypropylene plate of 2 mm thick was used as the plate 422. The partition member 403 was attached to an appropriate position 404 inside the vessel body 401. The inside of the vessel body 401 was partitioned into a first compartment 405 and a second compartment 406 by the partition member 403. A hole 407 was formed through the vessel cover 402 in order to lead a fluid delivery portion out of the vessel. An electrochemical cell portion 408 was attached to the bottom portion of the vessel body 401. The reference numeral 409 represents a power supply; 410, a switch; and 411, a gas introduction portion for introducing a gas generated from the electrochemical cell portion 408 into the second compartment 406. The gas introduction portion 411 was provided as a passageway in the bottom portion of the vessel body 401. Fittings 412 is used for fixedly connecting the vessel body 401 and the vessel cover 402 to each other. A transformable fluid reservoir 413 reserved a physiological salt solution 414 therein. The reference numeral 415 represents a fluid delivery pipe acting as the fluid delivery portion; 416, an injection needle; 417, a hole for discharging a gas to the outside; and 418, a valve for discharging a gas accumulated in the second compartment 406 after the completion of use. All the materials used herein, other than partition member, were the same as those in Example 1. As a result, if a current the same as that in Example 1 was made to flow, the physiological salt solution was delivered at the same rate.

If such a partition member is used, there are advantages that when, for example, a bladder used as a fluid reservoir is not one sheet formed by blow molding, but a laminated bladder produced by bonding two sheets at their outer peripheral portions through heat seal or the like, pressure can be used effectively if the pressure is given not horizontally but in vertically with respect to the sheet because there is an overlap width for the heat-seal portion. In addition thereto, the fluid delivery device after use is not bulky because the fluid reservoir is shrank like a plate, and the like.

As an electrochemical cell which can be used in the present invention, generally, any cell can be used so long as it can generate a gas proportionally to the quantity of electricity when a DC current is made to flow thereto. More specifically, the following cells can be used.

1) Porous metal electrodes are joined to both sides of a solid polymer cation exchange membrane respectively, and both the two electrodes are made to contact with water so as to use oxygen or hydrogen generated from an anode or cathode respectively upon current conduction, or a gas mixture of the oxygen and hydrogen.

2) Porous metal electrodes are joined to both sides of a solid polymer cation exchange membrane respectively, and the anode is made to contact with water while the cathode is made to contact with the air or oxygen, so that oxygen generated from the anode upon current conduction is used.

3) A porous metal electrode and a manganese (IV) oxide are joined to one and the other sides of a solid polymer cation exchange membrane as the anode and the cathode respectively, so that oxygen generated from the anode upon current conduction is used.

4) A porous metal electrode and a manganese (IV) oxide or a nickel (II) hydroxide are joined to one and the other sides of a solid polymer anion exchange membrane as the anode and the cathode respectively, so that oxygen generated from the anode upon current conduction is used.

5) Water is electrolyzed by use of any of various kinds of inorganic protonic conductors such as a dodeca molybdophosphoric acid ($H_3PMo_{12}O_{40} \cdot 29H_2O$), a hydrogen uranyl phosphate ($HUO_2PO_4 \cdot 4H_2O$), a hydrous antimony (V) oxide ($Sb_2O_3 \cdot H_2O$) and the like. Oxygen or hydrogen generated therein, or a gas mixture of both the oxygen and hydrogen is used.

In the fluid delivery device according to the present invention, the inside of the fluid delivery device body is partitioned into the first compartment and the second compartment by the partition member which can be transformed by the pressure of a gas, and the transformable fluid reservoir having the fluid delivery portion is disposed in the first compartment. Accordingly, when a gas generated in the electrochemical cell portion is introduced into the second compartment, the inner pressure of the second compartment increases to push the partition member so that a fluid reserved in the fluid reservoir is delivered through the fluid delivery portion by the pressure of the partition member. If the second compartment is kept air-tight, therefore, it is not necessary to keep the first compartment air-tight, and it is extremely easy to set the fluid reservoir into the vessel body so that the device can be ready for use in a short time. If the fluid reservoir is replaced by another one, it is possible to use one and the same device to deliver any of different kinds of fluids such as liquid medicines and the like.

Further, the fluid delivery device according to the present invention can be used repeatedly if a gas accumulated in the second compartment is released every time after use of the device.

In addition, polyethylene, polypropylene, neoprene rubber, or the like other than polyethylene terephthalate or polyvinyl chloride mentioned in the above embodiments can be used as the material of the partition member which can be transformed by the pressure of a gas and which is attached to the inside of the vessel body. The present invention is, however, not limited to those mentioned above. To select the material, it is necessary to take the condition into consideration that the material has a low permeability for oxygen or hydrogen generated from the electrochemical cell. In addition, the position where the partition member is attached is not limited to the position mentioned in the above embodiments, and may be attached to any appropriate position of a fluid delivery device body so long as the second compartment can be kept air-tight.

Although the electrochemical cell portion is attached to the bottom portion of the vessel body which is a portion of the fluid delivery device body in Example 1, the electrochemical cell portion may be attached to any position so long as a gas generated from the electrochemical cell portion can be introduced into the second compartment.

As it has been described above, the fluid delivery device according to the present invention can be made small in size, light in weight, and easy to operate during use. Particularly, for use for delivering a liquid medicine for medical treatment, the device is extremely easy for a patient to use. As it has been described above, the fluid delivery device according to the present invention has a simple structure, low in manufacturing cost, and easy to operate. In addition, it is possible to eliminate defects belonging to conventional bellows, diaphragms or a electrochemically driven drug dispensers. Accordingly, the device has an extremely great industrial value.

What is claimed is:

1. An electrochemical fluid delivery device comprising:

an electrochemical cell portion for generating a gas when supplied with a current; and a fluid delivery device body including:

a partition member which is transformable by a pressure of the gas;

a first and a second compartment which are formed in said fluid delivery device body by said partition member, said first compartment having at least one surface, wherein at least a part of said surface is removable;

a transformable fluid reservoir contained in said first compartment, said transformable fluid reservoir reserving a fluid to be delivered, said transformable fluid reservoir including a fluid delivery portion leading out of said first compartment; and a gas introduction portion for introducing the gas generated in said electrochemical cell portion into said second compartment;

wherein the gas generated in said electrochemical cell portion is introduced into said second compartment to increase an inner pressure of said second compartment to Press said Partition member, and the fluid being reserved in said transformable fluid reservoir is delivered through said fluid delivery Portion by the pressure of said partition member on said transformable fluid reservoir, wherein said first compartment includes at least one air gap.

* * * * *